United States Patent
Fukui et al.

(10) Patent No.: US 8,383,413 B2
(45) Date of Patent: Feb. 26, 2013

(54) METHOD FOR ANALYZING OLIGOMERIC PROANTHOCYANIDIN (OPC)

(75) Inventors: Yuko Fukui, Takatsuki (JP); Koichi Nakahara, Toyonaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 103 days.

(21) Appl. No.: 11/658,311

(22) PCT Filed: Jul. 27, 2005

(86) PCT No.: PCT/JP2005/014153
§ 371 (c)(1),
(2), (4) Date: Jan. 24, 2007

(87) PCT Pub. No.: WO2006/011640
PCT Pub. Date: Feb. 2, 2006

(65) Prior Publication Data
US 2008/0311662 A1    Dec. 18, 2008

(30) Foreign Application Priority Data
Jul. 29, 2004    (JP) .................................. 2004-222255

(51) Int. Cl.
*G01N 21/75*    (2006.01)

(52) U.S. Cl. ........................ 436/164; 436/93; 436/161

(58) Field of Classification Search .................. None
See application file for complete search history.

(56) References Cited

U.S. PATENT DOCUMENTS

| | | | |
|---|---|---|---|
| 191,131 | A | 5/1877 | Gainey |
| 402,738 | A | 5/1889 | Hyatt |
| 2,066,479 | A | 1/1937 | MacIsaac |
| 3,357,566 | A | 12/1967 | Schmid et al. |
| 3,568,414 | A | 3/1971 | Spriggs et al. |
| 4,002,567 | A | 1/1977 | Konno et al. |
| 4,060,483 | A | 11/1977 | Barzuza |
| 4,090,962 | A | 5/1978 | Braukmann |
| 4,692,247 | A | 9/1987 | Orlans |
| 5,236,126 | A | 8/1993 | Sawade et al. |
| 5,824,229 | A | 10/1998 | Larkey et al. |
| 6,267,879 | B1 | 7/2001 | Gil |
| 6,800,433 | B1 * | 10/2004 | Honda et al. .................. 435/4 |

FOREIGN PATENT DOCUMENTS

| | | |
|---|---|---|
| EP | 460842 | 12/1991 |
| JP | 2002-542240 | 12/2002 |
| WO | WO 00/63201 | 10/2000 |
| WO | WO 01/70214 A2 | 9/2001 |

OTHER PUBLICATIONS

English translation of Hiermann et al. Scientia Pharmaceutic, 1986, cited in Apr. 30, 2008 IDS.*

(Continued)

*Primary Examiner* — Robert Xu
(74) *Attorney, Agent, or Firm* — Drinker Biddle & Reath LLP

(57) ABSTRACT

The present invention provides a novel method for assaying OPC contained in natural substances, foods and beverages, pharmaceuticals and/or cosmetics.

The present invention is a novel method for assay of OPC which assays anthocyanidin, obtained by hydrolysis of OPC, to determine the total amount of OPC, and elucidates the proportions of the polymerization degrees of OPC by high performance liquid chromatography (HPLC) to determine the contents of the respective polymers in OPC.

22 Claims, 2 Drawing Sheets

OTHER PUBLICATIONS

Jende-Stride, Barbro, Phenolic acid in grains of wild-type barley and proanthocyanidin-free mutants, 1985, Carlsberg Research Communication, vol. 50, pp. 1-14.*

Waterhouse L. Andrew et al., A comparison of methods for quantifying oligomeric proanthocyanidins from grape seed extracts, 2000, American Journal of Enology and Viticulture, vol. 51(4), pp. 383-389.*

Filtomat, Inc. Advertisement "Water filter puts algae in their place," Grounds Maintenance, p. 56 (Oct. 1989).

Eagle Publications Advertisement "Filtration News, Special Emphasis: Filter Media Filtration 2002 Show Issue" Eagle Publications, Inc., pp. 17, 30 (Sep. 2002).

Zurn Industries, Inc. Owner's Catalogue "Self-Cleaning Pipeline Strainers" Zurn Industries, Inc. (Oct. 1974).

Sano et al., "Procyanidin B1 Is Detected in Human Serum after Intake of Proanthocyanidin-rich Grape Seed Extract," Biosci. Biotechnol. Biochem., 2003, vol. 67(5), pp. 1140-1143.

Gu et al., "Screening of Foods Containing Proanthocyanidins and Their Structural Characterization Using LC-MS/MS and Thiolytic Degradation," *Journal of Agricultural and Food Chemistry*, 2003, vol. 51, pp. 7513-7521, American Chemical Society, Columbus OH.

Japan Food Science, *January Issue*, 2004, vol. 403, pp. 40-45. (Japanese language).

Botha et al., "Synthesis of Condensed Tannins. Part 4†a Direct Biomimetic Approach to [4,6]- and [4,8]-Biflavanoids," 1981, pp. 1235-1245, J.C.S. Perkin I.

Pace-Asciak et al., "The red wine phenolics *trans*-resveratrol and quercetin block human platelet aggregation and eicosanoid synthesis: Implications for protection against coronary heart disease," *Clinica Chimica Acta*, 1995, vol. 235, pp. 207-219, Elsevier.

International Search Report dated Mar. 2, 2006 in International PCT Appln. No. PCT/JP2005/014153 (WO 2006/011640).

Ariga et al., "Isolation, Identification and Organoleptic Astringency of Dimeric Proanthocyanidins Occurring in Azuki Beans," Agric. Biol. Chem. 45(12), 1981, pp. 2709-2712.

Rychlińska et al., "Qualitative and Quantitative Chromatographic Investigation of Flavonoids in *Pyrus communis* L. Flowers," Acta Poloniae Pharmaceutica—Drug Research, vol. 60, No. 1, 2003, pp. 81-85.

Pérez-Ilzarbe et al., "Liquid Chromatographic Determination of Apple Pulp Procyanidins," Journal of Liquid Chromatography, 15(4), 1992, pp. 637-646.

Tomczyk et al., "Quantitative Analysis of Flavonoids in the Flowers and Leaves of *Ficarea verna* Huds," Journal of Biosciences, Tuebingen, DE., vol. 58, 2002, pp. 762-764.

Porter et al., "The Conversation of Procyanidins and Prodelphinidins to Cyanidin and Delphinidin," Phytochemistry, vol. 25, No. 1, 1986, pp. 223-230.

Office Action issued Feb. 4, 2008, by Intellectual Property Office of Singapore in application No. SG 200700632-3.

Hiermann et al., "A method for the quantitative determination of procyanidins in Crataegus," Scientia Pharmaceutic, vol. 54, 1986, pp. 331-337 (English-language abstract).

Japan Food Science, "Features and Antioxidative Effect of French Maritime Pine Polyphenol 'Flavangenol®'," *January Issue*, 2004, vol. 403, pp. 40-45. (w/partial English-language translation).

Treutter, "Chemical Reaction Detection of Catechins and Proanthocyanidins with 4-Dimethylaminocinnamaldehyde," Journal of Chromatography, vol. 467, 1989, pp. 185-193, Elsevier, Amsterdam, Holland.

Treutter et al., "Identification of flavan-3-ols and procyanidins by high-performance liquid chromatography and chemical reaction detection," Journal of Chromatography, vol. 667, 1994, pp. 290-297, Elsevier, Amsterdam, Holland.

Hiermann et al., "A method for the quantitative determination of procyanidins in *Crataegus*," Scientia Pharmaceutica, vol. 54, 1986, pp. 331-337 (English translation).

Bate-Smith, "Phytochemistry of Proanthocyanidins," Phytochemistry, 1975, vol. 14, pp. 1107-1113.

Taiwanese Office Action issued Mar. 25, 2011 in Taiwanese Application No. 094125641 (w/English language translation).

Wittig et al., "Quantification of procyanidins in Oral Herbal Medicinal Products Containing Extracts of *Crataegus* Species," Arznelm-Forsch/Drug Res. vol. 52, No. 2, pp. 89-96 (2002).

Svedström et al., "High-performance liquid chromatographic determination of oligomeric procyanidins from dimmers up to the hexamer in hawthorn," Journal of Chromatography A, vol. 968, pp. 53-60 (2002).

Monographie Weiβornfrüchte, in: Ph. Eur. 2000, pp. 1507-1508, Deutscher Apotheker Verlag, Stuttgart (2000) (in German, w/ English translation).

* cited by examiner

METHOD FOR ANALYZING OLIGOMERIC PROANTHOCYANIDIN (OPC)

CROSS REFERENCE TO RELATED APPLICATIONS

This application is the National Stage of International Application No. PCT/JP2005/014153, filed Jul. 27, 2005, and claims benefit of Japanese Application No. 2004-222255, filed Jul. 29, 2004, which is incorporated herein in its entirety.

TECHNICAL FIELD

This invention relates to a method for determining oligomeric proanthocyanidin (generic name for a mixture of n-polymers of flavan-3-ol: $n \geq 2$) contained in analytes or samples to be analyzed, such as naturally occurring substances, foods and drinks, pharmaceuticals and/or cosmetics.

BACKGROUND ART

Proanthocyanidin (OPC) is said to be one of the efficacious components of the French Paradox, since it is contained in wine as well (1995, Clin. Chim. Acta. 235, 207-219). An antioxidant action, a peripheral circulation improving action, a blood flow improving effect, a hepatic function improving effect (2004, Japan Food Science, 403, January Issue, 40-45), and a platelet aggregation suppressing effect (Officially Published Patent Gazette 2003-527418) are known as the medicinal benefits of proanthocyanidin. Development of a method for convenient qualitative and quantitative evaluation of OPC, which is such an active ingredient, is therefore desired.

Known methods for analyzing proanthocyanidin include reversed phase HPLC by high-performance liquid chromatography-mass spectrometry (LC-MS) (2003, Biosci. Biotechnol. Biochem., 67, (5), 1140-1142), and normal phase HPLC involving gradient elusion by LC-MS (2003, J. Agric. Food Chem., 51, 7513-7521). However, both of these methods require MS detectors, and none of them are said to be convenient. Furthermore, proanthocyanidin is present as very many stereoisomers, owing to the stereoisomerism of flavan-3-ols which are the constituents of proanthocyanidin. There are limits on the compounds available as standard substances. Thus, its quantitative analysis has been impossible, except for some known compounds. Besides, proanthocyanidin exists in the natural world in forms ranging from the monomer flavan-3-ol to a dimer, a trimer, and further to n-mers of a higher polymerization degree. The analysis by reversed phase HPLC has shown that peaks of flavan-3-ol (monomer), the dimer and the trimer overlap.

As described above, no convenient method has been existent for the qualitative and quantitative evaluation of OPC.

DISCLOSURE OF THE INVENTION

Under these circumstances, the inventors have focused attention on the desire for the development of a novel method of analysis which can determine the abundance ratios and contents of n-mers contained in natural substances, foods and beverages, and pharmaceutical products, without interference from flavan-3-ol which is the monomer. It is an object of the present invention, therefore, to provide a novel method for assaying OPC which is contained in analytes, such as natural substances, foods and beverages.

EFFECTS OF THE INVENTION

Figure 1:
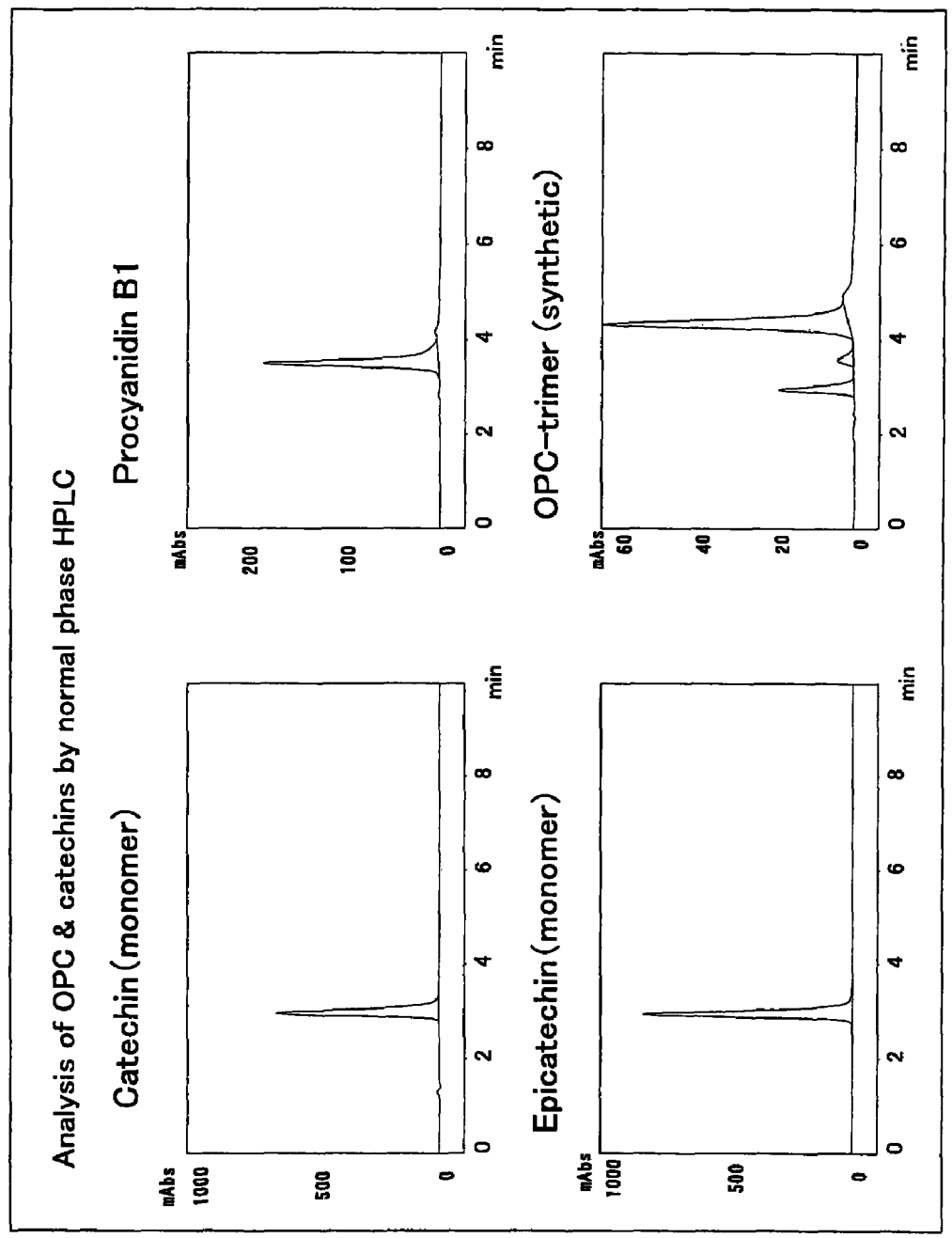
FIG. 1 is a view showing the results of analysis of catechin, and a dimer and a trimer of flavan-3-ol by normal phase HPLC.

The inventors conducted various studies in an attempt to solve the aforementioned problems. As a result, they have elucidated, from the aspects of experimentation and molecular weight, that (a) the number of anthocyanidins produced by hydrolysis of oligomeric proanthocyanidin (OPC) is always n/2, regardless of the magnitude of the polymerization degree, n, of flavan-3-ol contained in OPC. This has led them to work out a convenient method of OPC assay. The inventors have further found the unexpected fact that (b) the separation of flavan-3-ol polymers of different polymerization degrees n, which have hitherto been difficult to separate by chromatography, can be easily achieved by high performance liquid chromatography using a normal phase column.

The method of the present invention uses the above fact (a) and/or the fact (b) to analyze the amount of oligomeric proanthocyanidin (OPC) in natural substances, foods and beverages, pharmaceuticals and/or cosmetics, and also analyze the proportions and/or contents of n-polymers in OPC in a convenient manner.

According to the method of the present invention, oligomeric proanthocyanidin (OPC) can be assayed without interference from the flavan-3-ol monomer often contained in oligomeric proanthocyanidin.

Also, the method of the present invention can assay flavan-3-ol polymers for respective polymers of oligomeric proanthocyanidin in analytes, without requiring a mass spectrometer. Thus, this method is very suitable for the analysis of oligomeric proanthocyanidin in natural substances, foods and beverages, pharmaceuticals and/or cosmetics.

MODES FOR CARRYING OUT THE INVENTION

The analytes targeted by the method of the present invention are arbitrary samples, which are expected to contain a mixture of n-polymers ($n \geq 2$) of flavan-3-ol (hereinafter referred to as oligomeric proanthocyanidin or OPC), such as natural substances (grape seeds, tamarind, apple, bark, pine bark-derived polyphenol, tea leaves, cocoa, etc., and/or their treatment products (extract, etc.)), foods and beverages, pharmaceuticals and/or cosmetics.

Oligomeric proanthocyanidin, typically, includes at least one of compounds represented by the following general formulas:

[Chemical formulas 1]

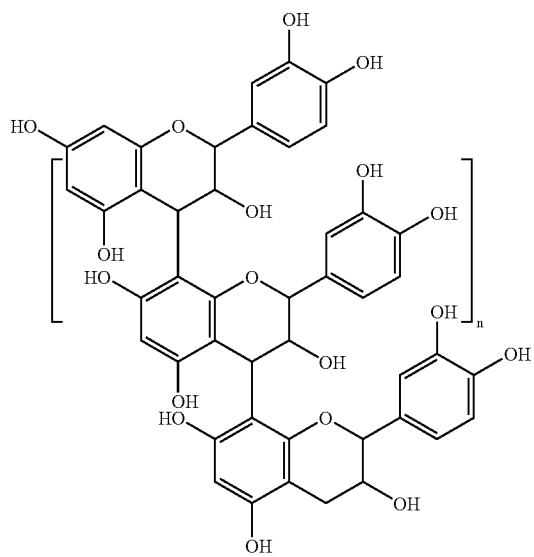

Structural formula 1

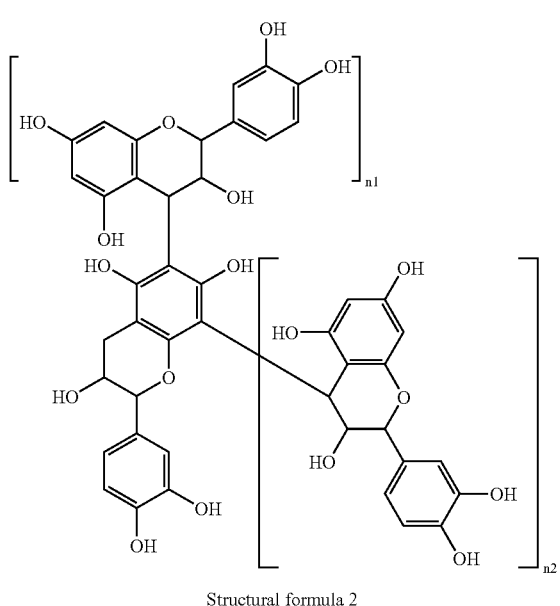

Structural formula 2

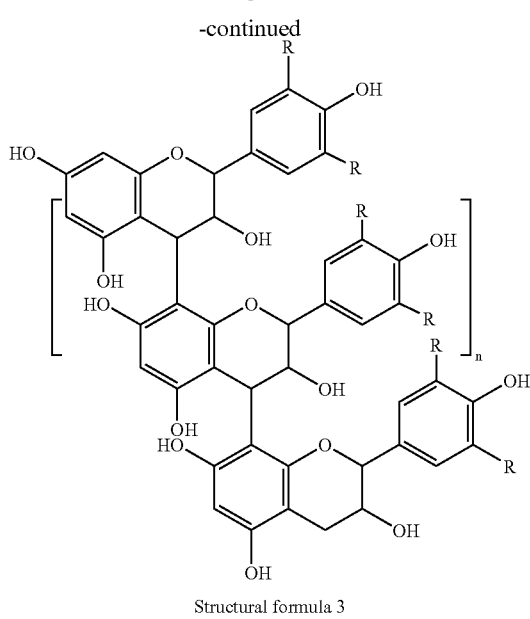

Structural formula 3

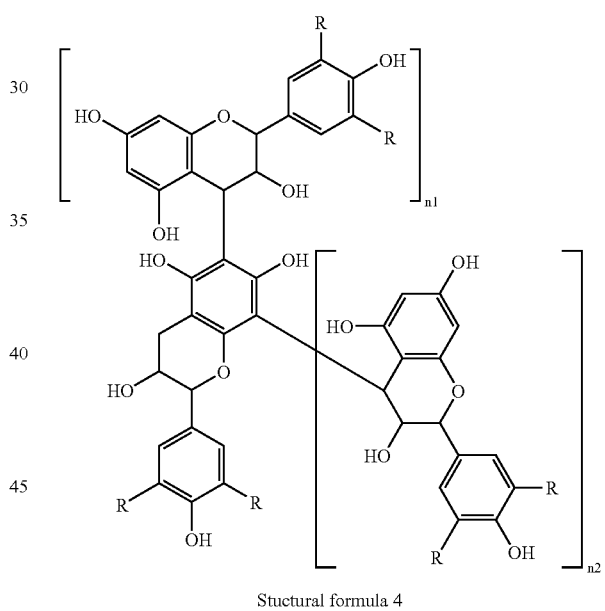

Stuctural formula 4 n = integer of 0 to 18,
n1 = integer of 1 to 18,
n2 = integer of 0 to 18, and
R = H or OH The present invention targets, particularly, the above oligomeric proanthocyanidin which is proanthocyanidins including at least one of procyanidins B1, B2, B3 and B4 of the structural formula 1 where n=0, procyanidins B5, B6, B7 and B8 of the structural formula 2 where n1=1 and n2=0, and procyanidins C1, C2 and C4 of the structural formula 1 where n=1. The above B1, B2 . . . C1, C2 . . . are stereoisomers of the respective compounds. The structures of the main procyanidins, OPC and catechin are illustrated below.

[Chemical formulas 1a]

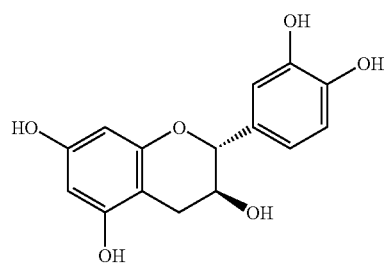

Catechin

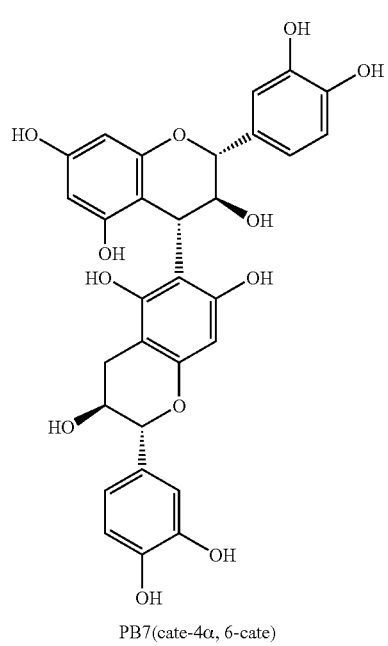

PB7(cate-4α, 6-cate)

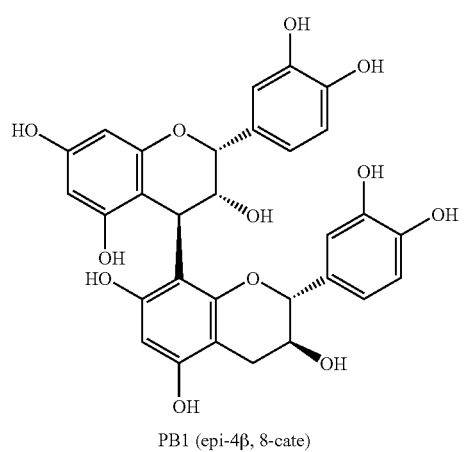

PB1 (epi-4β, 8-cate)

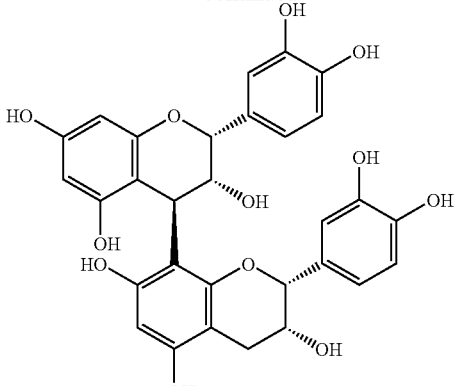

PB2 (epi-4β, 8-epi)

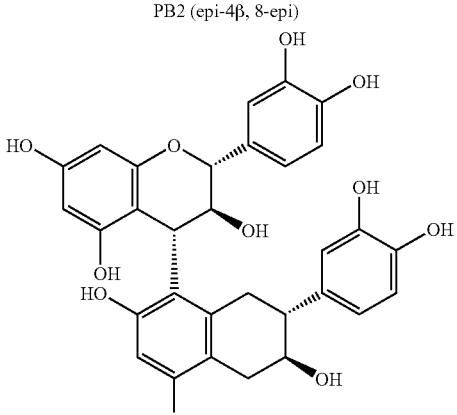

PB3 (cate-4α, 8-cate)

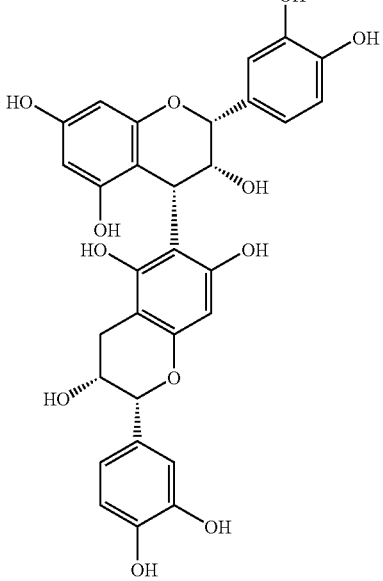

PB5 (epi-4β, 6-epi)

(1) Determination of Total Amount of OPC

According to the present invention, there is no need to consider the types and polymerization degrees of flavan-3-ol polymers contained in oligomeric proanthocyanidin (OPC) in analytes and, when anthocyanidin occurring upon hydrolysis of OPC is assayed, the total amount of OPC can be determined from its value. The method of the present invention can be performed in the following sequence:

Hydrolysis of OPC

The hydrolysis of oligomeric proanthocyanidin can be performed by thermal decomposition under acidic conditions. The preferred conditions include, for example, the use of an acid/lower alcohol mixture as acidic conditions, the acid being preferably hydrochloric acid, sulfuric acid or nitric acid, and the lower alcohol being preferably propanol, butanol, pentanol and/or isopentanol. The thermal decomposition can be performed, with the temperature being 50 to 100° C., preferably 80 to 100° C., more preferably 85 to 95° C., and the reaction time being 30 minutes or more, preferably 1 hour or more. The concentration of the acid can be chosen from the range of 0.1 N to 2 N, preferably 0.4 N to 1 N.

In performing hydrolysis, if the analyte is a liquid sample containing oligomeric proanthocyanidin in a low concentration, the sample may be concentrated by a suitable method, for example, lyophilization or drying or solidification to dryness under reduced pressure.

The analyte (including the concentrate) is dissolved in the above-mentioned acid/lower alcohol mixture at a concentration of 0.01 to 1%, preferably, 0.05 to 0.21 (0.5 to 2 mg/ml), whereby it can be hydrolyzed.

A concrete example of the hydrolysis is as follows: A sample (0.5 mg) containing proanthocyanidin is dissolved in 1 ml of 0.6N HCl/butanol in a glass test tube, and the solution is allowed to stand for 2 hours in a water bath at 90° C. After completion of the reaction, the absorption spectrum at 700 to 400 nm is measured with UV-265 (Shimadzu Corp.). Measurement of the absorbance at 551 nm confirms whether the hydrolysis reaction has been fully carried out to produce anthocyanidin.

Measurement of Amount of Anthocyanidin

The measurement of the amount of anthocyanidin produced by hydrolysis may be made by any publicly known method and, for example, can be performed easily by high performance liquid chromatography or the absorbance method. The absorbance method can be performed using the hydrolyzate unchanged and, preferably, measures the absorbance at 550 to 552 nm at which anthocyanidin shows a maximum absorption in the visible absorption spectrum. At this wavelength, the influence of components other than anthocyanidin produced by the hydrolysis of oligomeric proanthocyanidin (e.g., catechin: maximum absorption 270 nm) can be disregarded.

An example of the HPLC process is concretely described as follows: Anthocyanidin is assayed using an HPCL column YMC-ODS-A312 (6 mm×150 mm, YMC), 1 ml/min of a mixture acetic acid:methanol:water=15:17.5:67.5, and a column temperature of 40° C., with an area value at A520 nm being detected. Cyanidin chloride, delphinidin chloride, and pelargonidin chloride (all available from Funakoshi) can be used as standard substances. The retention times of these standard substances are all different, and a mixture of them or any one of them selected can be used as a standard substance. As the HPLC column, not only the above C18-based resin, but also the C8-, C30-, or polymer-based C18 resin can make analysis similarly, as long as it is a reversed phase resin.

Calculation of Total Amount of OPC

To determine the amount of oligomeric proanthocyanidin in the analyte based on the amount of anthocyanidin assayed above, the following procedure is, effected: a) The amount of anthocyanidin produced from one n-polymer by hydrolysis is n/2, regardless of the magnitude of the polymerization degree n of the flavan-3-ol polymer contained in OPC. Based on this fact, the amount of anthocyanidin produced by hydrolysis is multiplied by a factor 2, whereby the total amount of OPC in a predetermined amount of the analyte can be found, for example, in mg. Alternatively, b) the amount of anthocyanidin produced by hydrolysis of OPC is in proportion to the total amount of OPC, regardless of the magnitude of the polymerization degree n of the flavan-3-ol polymer contained in OPC. Based on this fact, the amount of anthocyanidin produced by hydrolysis is compared with the amount of anthocyanidin produced by hydrolysis of a known amount of an OPC standard substance, and the total amount (e.g., in mg) of OPC in the analyte and/or the proportion (a %) of OPC in the analyte can be determined by a calibration curve or the following equation:

Total amount of OPC (mg)=(measured value of sample/measured value of standard)×amount (mg) of standard       (Equation 1)

Proportion ($a$%) of OPC in analyte=(total amount (mg) of OPC/amount of analyte)×100       (Equation 2)

The standard substance used can be selected, as appropriate, from procyanidin B1 and procyanidin B2 (both available from Funakoshi).

(2) Assay of Each of N-Polymers Constituting OPC

In particularly preferred embodiments of the present invention, in addition to or separately from the determination of the total weight of OPC in the predetermined weight of the analyte in (1) above, the proportions of various flavan-3-ol polymers in OPC are clarified by high performance liquid chromatography (HPLC). By so doing, there is also provided a novel method of OPC assay which determines the weights of respective polymers of different polymerization degrees, n, contained in the predetermined weight of the analyte.

The column used in the high performance liquid chromatography is preferably a normal phase column, and particularly preferably a normal phase column packed with a silica gel-based resin. Studies by the inventors have shown that proanthocyanidin having different polymerization degrees (in this case, n=1 is also included) can be separated into constituents very satisfactorily by chromatography on a normal phase column. Judging from the fact that flavan-3-ols have high polarity, it has not been considered so far that they can be separated by a normal phase column. Furthermore, the method of the present invention enables measurement with the use of an ultraviolet detector, and does not require a mass spectrometric detector.

The conditions for high performance liquid chromatography may be determined as desired. If they are concretely illustrated, Inertsil SIL (4.6 mmφ×150 mm, GL Sciences Inc.), for example, is used as the column, the eluant is, for example, a mixture of hexane, methanol, tetrahydrofuran, and formic acid. Preferably, isocratic elution (about 1 ml/min) with hexane:MeOH:THF:HCOOH=45:40:14:1 is performed. Analysis can be made even at a flow velocity of 0.3 to 1.5 ml/min with the use of hexane:MeOH:THF:HCOOH=40-60:30-50:10-20:0.1-5. The column temperature is 10 to 60° C., preferably 40° C., and the detector is preferably a photodiode array detector, which is used in the collection of spectrum data at 240 to 400 nm. This is because OPC has a maximum absorption at 280 nm, but in the case of a sample incorporating other polyphenols in mixed form, different peaks at wavelengths other than 280 nm constitute the maximum absorption, thus making it possible to distinguish the other polyphenols from OPC and exclude them. However, in an environment where only a detector of a single wavelength can be used, analysis can be made only with the absorption at A280 nm.

The total peak area of all polymers separated by chromatography (all polymers including a dimer or polymers of higher degrees of polymerization) is the sum of the area values at A280 nm of peaks having the maximum absorption at 280 nm. The column may be Shimpack PREP-SIL(H) (4.6 mmϕ×300 mm, Shimadzu Corp.) or Supersher Si60 (4.5 mm×100 mm, Merck & Co.) as well as Inertsil SIL (4.6 mmϕ×150 mm, GL Sciences Inc.).

The proportion of each n-polymer constituting OPC (b %) can be calculated from the following equation based on the peak area obtained upon high performance liquid chromatography:

$$b\% = \{\text{peak area (each } n\text{-polymer)}\}/\{\text{total peak area (all polymers)}\} \times 100 \quad \text{(Equation 3)}$$

Based on the so obtained proportion of each n-polymer and the weight of OPC obtained in the aforementioned (1), the weight of each n-polymer contained in the predetermined weight of the analyte can be determined, for example, in mg by the following equation:

$$\text{Amount of } n\text{-polymer (mg)} = \text{total amount of OPC (mg)} \times \text{proportion of } n\text{-polymer } (b\%)/100 \quad \text{(Equation 4)}$$

Next, the present invention will be described more concretely by Examples. However, the present invention is not limited to these Examples.

EXAMPLE 1

Investigation of Acid Hydrolysis Conditions

The decomposition of flavangenol by acid was observed over time. Flavangenol (1 mg) was dissolved in 1 ml of 0.6N HCl/BuOH, and the solution was heated in a hot water bath at 90° C. After a lapse of 20 minutes until 140 minutes later, sampling was done at intervals of 20 minutes. The sample taken was diluted 1:10 with butanol, and measured for the visible absorption spectrum at 400 to 700 nm. The maximum absorption was present at 551 nm for all samples. The results of the measurements are shown in Table 1.

TABLE 1

Changes over time in acid-decomposed flavangenol

| Time | Absorbance (551 nm) |
|---|---|
| 20 min | 0.732 |
| 40 min | 0.796 |
| 60 min | 0.819 |
| 80 min | 0.830 |
| 100 min | 0.867 |
| 120 min | 0.877 |
| 140 min | 0.823 |

The outcome was that the absorbance increased slowly with the passage of time during acid decomposition, and reached its peak in 120 minutes. Based on this outcome, the period of hydrolysis was set at 120 min (2 hours) in subsequent experiments.

EXAMPLE 2

Production and Assay of Anthocyanidin Upon Acid Hydrolysis

A sample (0.5 mg) containing proanthocyanidin was dissolved in 1 ml of 0.6N HCl/butanol in a glass test tube, and the solution was allowed to stand for 2 hours in a water bath at 90° C. After completion of the reaction, the absorption spectrum at 700 to 400 nm was measured with UV-265 (Shimadzu Corp.), and the absorbance at 551 nm was determined. The solution after completion of the reaction was subjected to HPLC under the following conditions to assay anthocyanidin:

Column: YMC-ODS-A312, 6 mmϕ×150 mm
Mobile phase: $CH_3COOH:MeOH:H_2O=15:17.5:67.5$
Detection: A520 nm (measured at 400 to 600 nm by PDA)

As standard substances for assay, delphinidin, cyanidin and pelargonidin were purchased from Funakoshi. The standard substance, delphinidin, was eluted in 4.2 minutes, with λmax of 535 nm, cyanidin was eluted in 5.5 minutes, with λmax of 525 nm, and pelargonidin was eluted in 8.0 minutes, with λmax of 515 nm. The components from the acid hydrolyzate of the sample, corresponding to these conditions, were assayed as delphinidin, cyanidin and pelargonidin.

The samples analyzed were flavangenol, grape seed polyphenol, tea polyphenol, apple polyphenol, and tamarind, and procyanidin B1 (Funakoshi) was used as the standard substance for OPC.

The results are shown in Tables 2 and 3.

TABLE 2

OPC content by absorbance method

| | A550 nm | OPC content |
|---|---|---|
| Procyanidin B1 | 1.6905 | 100.0% |
| Flavangenol | 0.8897 | 52.6% |
| Apple | 0.3804 | 22.5% |
| Grape seeds | 0.7523 | 44.5% |
| Tamarind | 0.7641 | 45.2% |

TABLE 3

OPC content by HPLC method

| Sample | Cyanidin μg/ml | OPC content |
|---|---|---|
| Procyanidin B1 | 66.19 | 100.0% |
| Flavangenol | 29.45 | 44.5% |
| Tamarind | 28.64 | 43.3% |
| Apple | 13.48 | 20.4% |
| Grape seeds | 27.81 | 42.0% |
| Green tea | 1.84 + 1.98* | 5.8% |

*cyanidin 1.84 μg/ml + delphinidin 1.98 μg/ml

EXAMPLE 3

Analysis of Catechin, Dimer and Trimer by Normal Phase HPLC

The standard substances for catechin and prbanthocyanidin were analyzed by normal phase HPLC under the following conditions:

Samples (0.1 mg each) of (+)-catechin (Nacalai Tesque), (−)-epicatechin (Wako Pure Chemical Industries), and procyanidin B1 (Funakoshi) were each dissolved in 1 ml of a mobile phase, and the solution was filtered through a 0.45 μm filter, and then subjected to HPLC under the conditions shown below.

The trimer was synthesized by the method described in Example 5 to be offered below.

Column: Inertsil SIL, 4.6 mmϕ×150 mm
Mobile phase: hexane:MeOH:THF:HCOOH=45:40:14:1
Detection: A280 nm (measured at 240 to 400 nm by PDA)

Under these conditions, the monomers ((+)-catechin and (−)-epicatechin) were eluted in 2.9 minutes, the dimer in 3.6 minutes, and the trimer in 4.3 minutes.

Their chromatograms are shown in FIG. 1.

EXAMPLE 4

Analysis by Normal Phase HPLC

Samples containing catechin and proanthocyanidin in mixed form were analyzed by normal phase HPLC under the conditions shown below.

The sample (1 to 2 mg) containing proanthocyanidin was dissolved in 1 ml of a mobile phase, and the solution was filtered through a 0.45 μm filter, and then subjected to HPLC under the following conditions.

The samples used were apple polyphenol, grape seed polyphenol, flavangenol, and tamarind.

Column: Inertsil SIL, 4.6 mmφ×150 mm
Mobile phase: hexane:MeOH:THF:HCOOH=45:40:14:1
Detection: A280 nm (measured at 240 to 400 nm by PDA)

Figure 2:
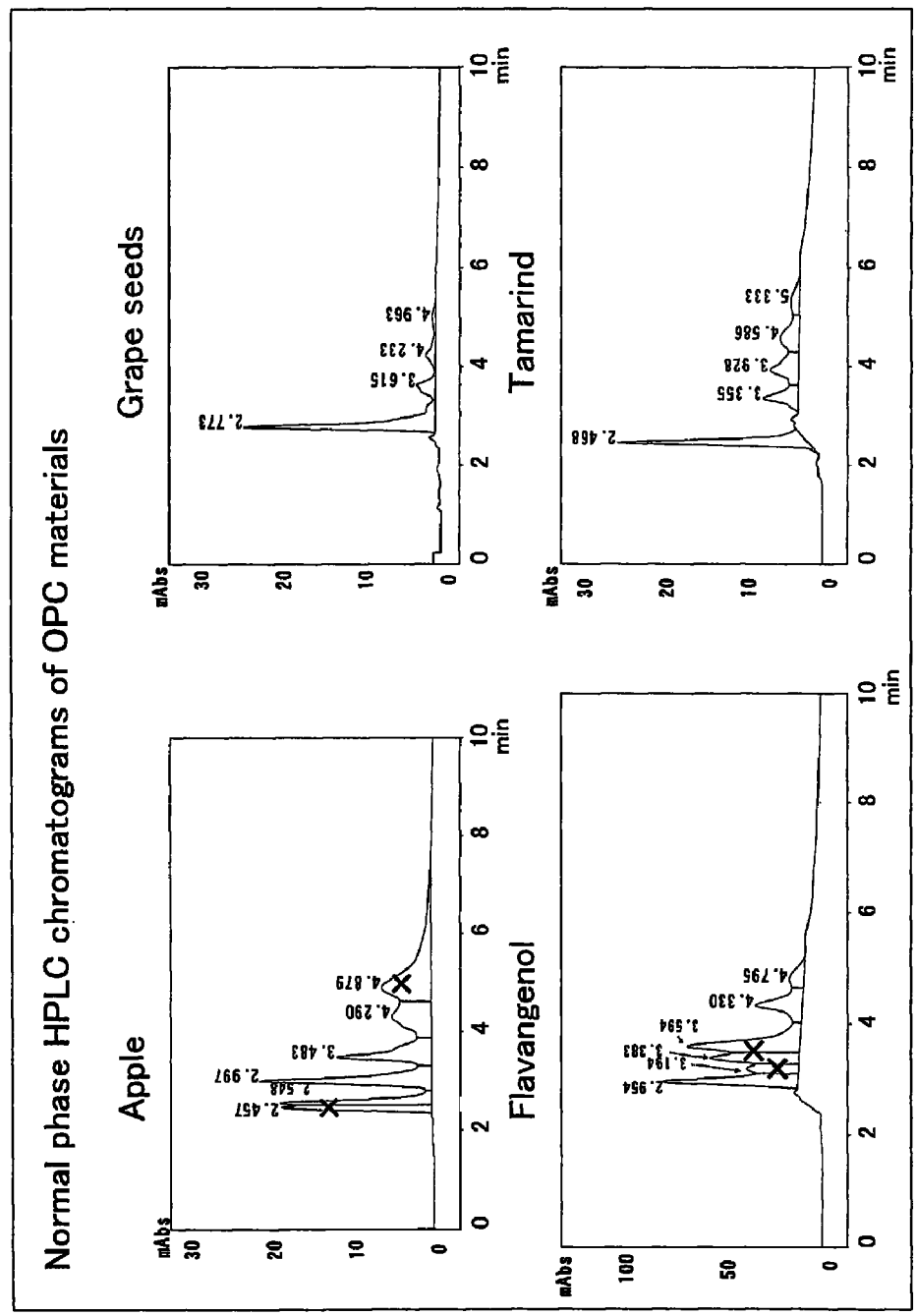
FIG. 2 is a view showing the results of analysis of analytes, which have catechin and proanthocyanidin mixed therein, by normal phase HPLC.

The chromatograms as analytic patterns are shown in FIG. 2. In these patterns, the symbol x represents polyphenols having no maximum absorption at 280 nm and different from OPC.

The concentrations of the dimer and the trimer in each sample were determined by the equation c %=a %×b %. The results are shown in Table 4.

TABLE 4

Contents of dimer and trimer

| | OPC purity a % | | A280 nm ratio b % | Abundance ratio c % |
|---|---|---|---|---|
| Flavangenol | 44.5% | Dimer | 55.4% | 24.7% |
|  | 44.5% | Trimer | 32.0% | 14.2% |
| Apple polyphenol | 20.4% | Dimer | 31.6% | 6.4% |
|  | 20.4% | Trimer | 23.5% | 4.8% |
| Grape seed polyphenol | 42.0% | Dimer | 12.5% | 5.3% |
|  | 42.0% | Trimer | 5.8% | 2.4% |
| Tamarind | 43.3% | Dimer | 22.8% | 9.9% |
|  | 43.3% | Trimer | 23.2% | 10.0% |

EXAMPLE 5

Synthesis of OPC

The synthesis of OPC was performed in the following manner in accordance with a paper (1981, J.C.S. Perkin I. 1235-1245).

(+)-Taxifolin (500 mg) was dissolved in 50 ml of ethanol, and 200 mg of $NaBH_4$ was added. Then, 1 g of (+)-catechin was added and dissolved. Then, HCl was added, and the mixture was stirred for 1 hour. The reaction product was purified by reversed phase HPLC to obtain a trimer.

The invention claimed is:

1. A method for determining a total weight of a mixture of n-polymers ($n \geq 2$) of flavan-3-ol (oligomeric proanthocyanidin or OPC) contained in a predetermined weight of a sample, said method comprising measuring a weight of anthocyanidin produced by hydrolysis of OPC in the sample, separately measuring an amount of anthocyanidin produced by hydrolysis of a known weight of a standard substance, wherein the standard substance is an OPC standard substance or a n-polymer ($n \geq 2$) of flavan-3-ol, and determining the total weight of OPC in the sample and/or a weight ratio of OPC (a %) in the sample by a calibration curve or the following equation based on a fact that an amount of anthocyanidin produced by hydrolysis of OPC is in proportion to the total amount of OPC, regardless of an amount ratio of n-polymers contained in OPC and different in a magnitude of a polymerization degree n, and a complete hydrolysis reaction of a n-polymer ($n \geq 2$) of flavan-3-ol generates n/2 molecules of anthocyanidin:

Total weight of OPC=(measured value of sample/measured value of standard)×weight of standard substance　　(Equation 1)

Weight ratio of OPC (a %) in sample=(total weight of OPC/weight of sample)×100　　(Equation 2), wherein the mixture of n-polymers ($n \geq 2$) of flavan-3-ol of the sample is different from that of the standard substance.

2. The method according to claim 1, wherein the standard substance is procyanidin B1.

3. The method according to claim 1, wherein the hydrolysis is performed by thermal decomposition under acidic conditions.

4. The method according to claim 3, wherein the acidic conditions are a mixture of an acid and a lower alcohol.

5. The method according to claim 3 or 4, wherein the acid is hydrochloric acid, sulfuric acid, or nitric acid.

6. The method according to claim 4, wherein the lower alcohol is propanol, butanol, pentanol and/or isopentanol.

7. The method according to claim 3, wherein the thermal decomposition is performed at a temperature of 50 to 100° C., for a reaction time of 30 minutes or more.

8. The method according to claim 1, wherein the measurement of the amount of anthocyanidin is made by high performance liquid chromatography and/or an absorbance method.

9. The method according to claim 8, wherein the absorbance method is performed by measuring absorbance at 550 to 552 nm at which anthocyanidin shows a maximum absorption in a visible absorption spectrum.

10. A method for assaying oligomeric proanthocyanidin (OPC), contained in a sample, for n-polymers of flavan-3-ol different in a polymerization degree n, and comprising the steps of:
    a) determining a total weight of OPC, contained in a predetermined weight of the sample, by the method of claim 1;
    b) separately from the step a), analyzing the sample by high performance liquid chromatography (HPLC) to separate respective n-polymers of different polymerization degrees, n, contained in OPC, and determining quantitative proportions of the respective n-polymers to an amount of all n-polymers, namely, OPC, without any chemical modification of any of the n-polymers; and
    c) determining a weight of each n-polymer in the sample by results of a) and b).

11. The method according to claim 10, wherein a column used in the high performance liquid chromatography is a normal phase column.

12. The method according to claim 11, wherein a resin packed in the normal phase column is a silica gel-based resin.

13. The method according to claim 11, wherein, in the high performance liquid chromatography, an eluant is a mixture of hexane, methanol, tetrahydrofuran, and formic acid, a mixing ratio of the mixture is hexane/methanol/tetrahydrofuran/formic acid=40-60:30-50:10-20:0.1-5, a column temperature is 10 to 60° C., and an absorbance at 280 nm is measured.

14. The method according to claim 10, wherein the quantitative proportion of each n-polymer (b %) is calculated from the following equation based on a peak area obtained upon the high performance liquid chromatography:

$b$ %={peak area (each $n$-polymer)}/{total peak area (all polymers)}×100　　(Equation 3).

15. The claim according to claim 10, wherein the weight of each n-polymer in the step (c) is determined by the following equation based on the weight of OPC determined by (a) and the proportion of each n-polymer determined by (b):

Amount of $n$-polymer (mg)=total weight of OPC (mg)×proportion of $n$-polymer ($b$ %)/100　　(Equation 4).

16. The method according to claim 1, wherein the oligomeric proanthocyanidin to be assayed contains at least one of compounds represented by the following general formulas:
[Chemical formulas 1]
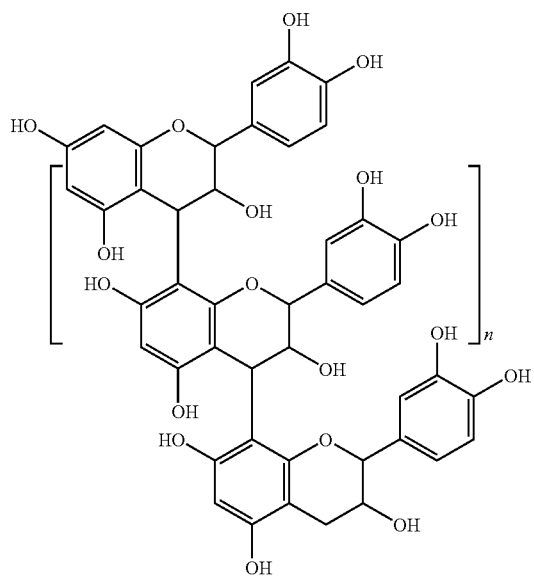
Structural formula 1
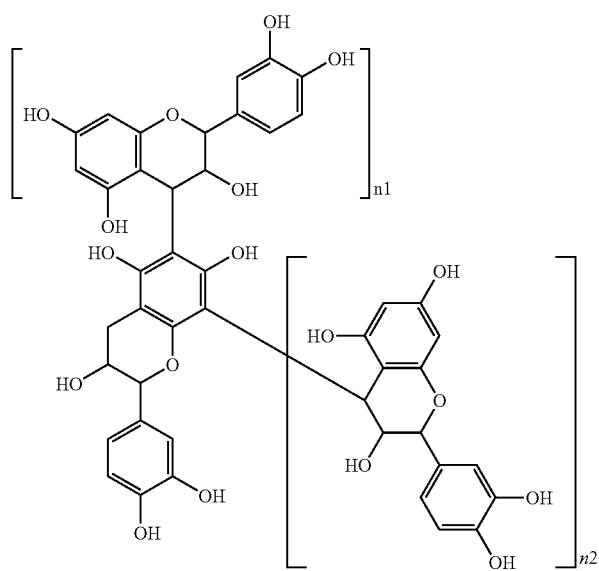
Structural formula 2

-continued

Structural formula 3

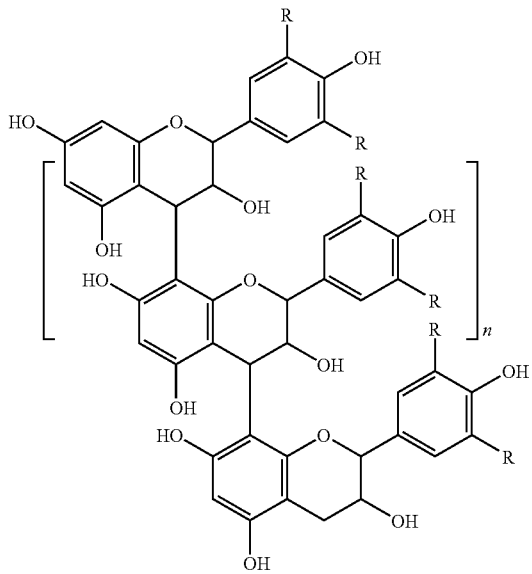

Structural formula 4

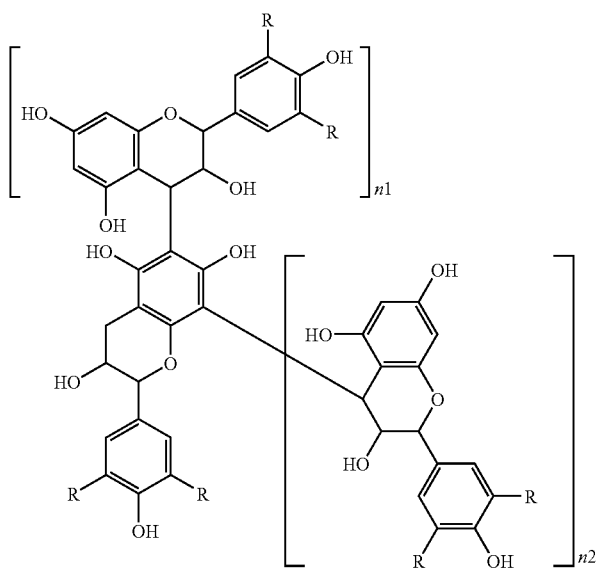

n = integer of 0 to 18,
n1 = integer of 1 to 18,
n2 = integer of 0 to 18, and
R = H or OH.

17. The method according to claim 16, wherein the oligomeric proanthocyanidin is proanthocyanidins containing at least one of procyanidins B1, B2, B3 and B4 of Structural Formula 1 where n=0, procyanidins B5, B6, B7 and B8 of Structural Formula 2 where n1=1 and n2=0, and procyanidins C1, C2 and C4 of Structural Formula 1 where n=1.

18. The method according to claim 1, wherein the sample is a natural substance comprising OPC.

19. The method according to claim 1, wherein the sample is a liquid including a soft drink or a refreshing drink, a tea beverage, or an alcoholic beverage, further comprising a step of lyophilizing the sample, or solidifying the sample to dryness under reduced pressure, followed by powdering.

20. The method according to claim 7, wherein the thermal decomposition is performed at a temperature of 85 to 100° C., for a reaction time of 1 hour or more.

21. The method according to claim 13, wherein the mixing ratio of the mixture is hexane/methanol/tetrahydrofuran/formic acid=45:40:14:1 in isocratic elution, and wherein the column temperature is 40° C.

22. The method according to claim 3, wherein the concentration of the acid is 0.1 N to 2 N.

* * * * *